United States Patent [19]

Coates et al.

[11] Patent Number: 4,774,032
[45] Date of Patent: Sep. 27, 1988

[54] VAPORIZERS AND WICK ASSEMBLIES THEREFOR

[75] Inventors: John R. Coates, Abingdon; Ralph J. East, Drayton Abingdon; Basil R. Sugg, Oxford, all of England

[73] Assignee: Penlon Limted, Abingdon, England

[21] Appl. No.: 2,650

[22] PCT Filed: Apr. 28, 1986

[86] PCT No.: PCT/GB86/00227

§ 371 Date: Dec. 17, 1986

§ 102(e) Date: Dec. 17, 1986

[87] PCT Pub. No.: WO86/06283

PCT Pub. Date: Nov. 6, 1986

[30] Foreign Application Priority Data

Apr. 29, 1985 [GB] United Kingdom ......... 8510805

[51] Int. Cl.⁴ ............................................. B01F 3/04
[52] U.S. Cl. .......................... 261/104; 261/DIG. 65; 128/204.13; 29/445; 228/155; 228/182
[58] Field of Search ............... 261/104, DIG. 65; 55/520; 128/204.13; 210/497.1, 493.4; 29/163.5 F, 445; 228/155, 182

[56] References Cited

U.S. PATENT DOCUMENTS

| | | | |
|---|---|---|---|
| 1,693,958 | 12/1928 | Patten | 55/520 |
| 2,610,038 | 9/1952 | Phillips | . |
| 2,879,979 | 3/1959 | Wheeler | 261/92 |
| 3,208,131 | 9/1965 | Ruff et al. | 29/163.5 F |
| 3,323,963 | 6/1967 | Summers | 210/493.4 |
| 3,346,933 | 10/1967 | Lindsay | 228/182 |
| 3,413,782 | 12/1968 | Bartlett | 55/520 |
| 3,479,731 | 11/1969 | Mantel et al. | 228/182 |
| 3,638,926 | 2/1972 | Melville et al. | . |
| 3,878,594 | 4/1975 | Minon, Jr. | 29/163.5 F |
| 3,954,920 | 5/1976 | Heath | . |
| 4,017,566 | 4/1977 | Seidel | 261/56 |
| 4,059,657 | 11/1977 | Hay | 261/104 |
| 4,521,947 | 6/1985 | Nonmenmann et al. | 228/182 |
| 4,618,462 | 10/1986 | Fisher | 261/104 |

FOREIGN PATENT DOCUMENTS

| | | | |
|---|---|---|---|
| 626687 | 10/1961 | Italy | 261/112.2 |
| 61-180842 | 8/1986 | Japan | 261/104 |
| 86720 | 10/1920 | Switzerland | 261/104 |
| 1043110 | 9/1966 | United Kingdom | . |

Primary Examiner—Tim Miles
Attorney, Agent, or Firm—Foley & Lardner, Schwartz, Jeffery, Schwaab, Mack, Blumenthal & Evans

[57] ABSTRACT

A wick assembly (1) for use in e.g. an anaesthetic vaporizer (not shown) comprises layer (2) of absorbent wick material, e.g. a metallic wire cloth, secured to an impermeable backing sheet (3) e.g. of stainless steel. The wick material (2) and backing sheet (3) are rolled into a spiral configuration and thus define a spiral flow passage for gas to be vaporized. Fastening means are provided to hold the wick material (2) and sheet (3) in the spiral configuration whereby the assembly forms a self-contained unit adapted to be detachably mounted in a vaporizer.

21 Claims, 3 Drawing Sheets

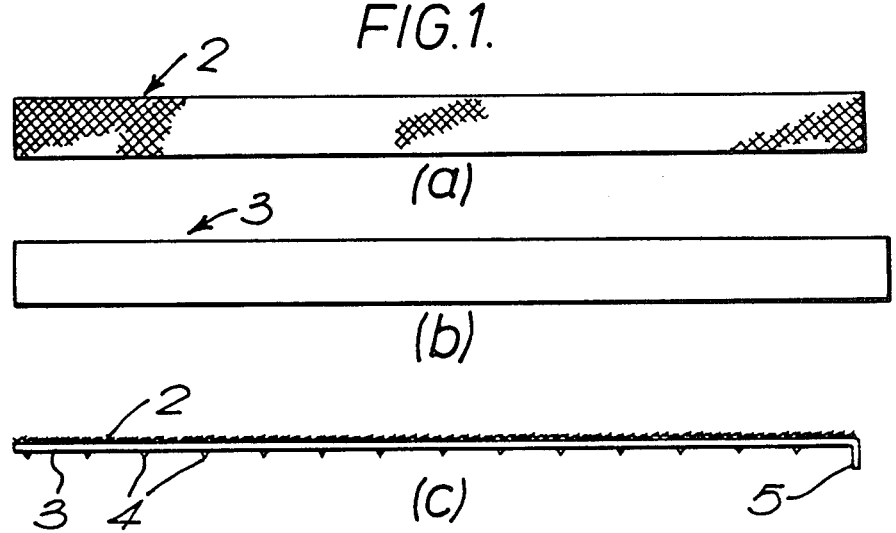
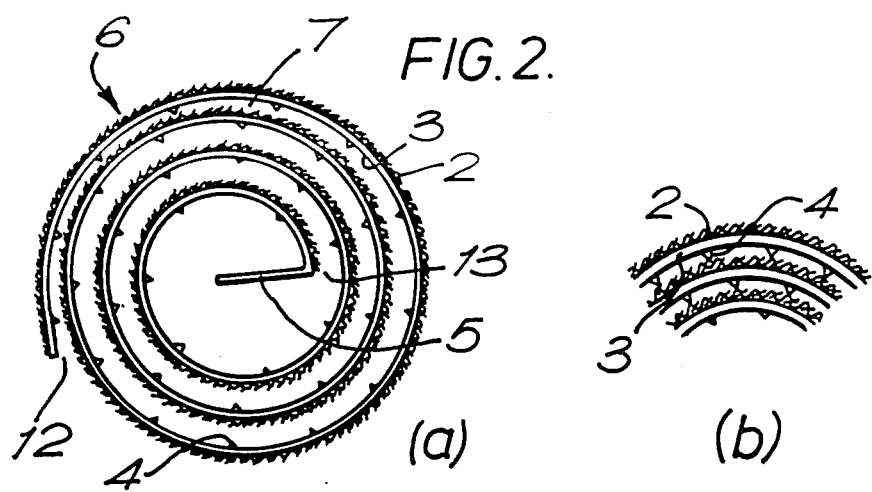

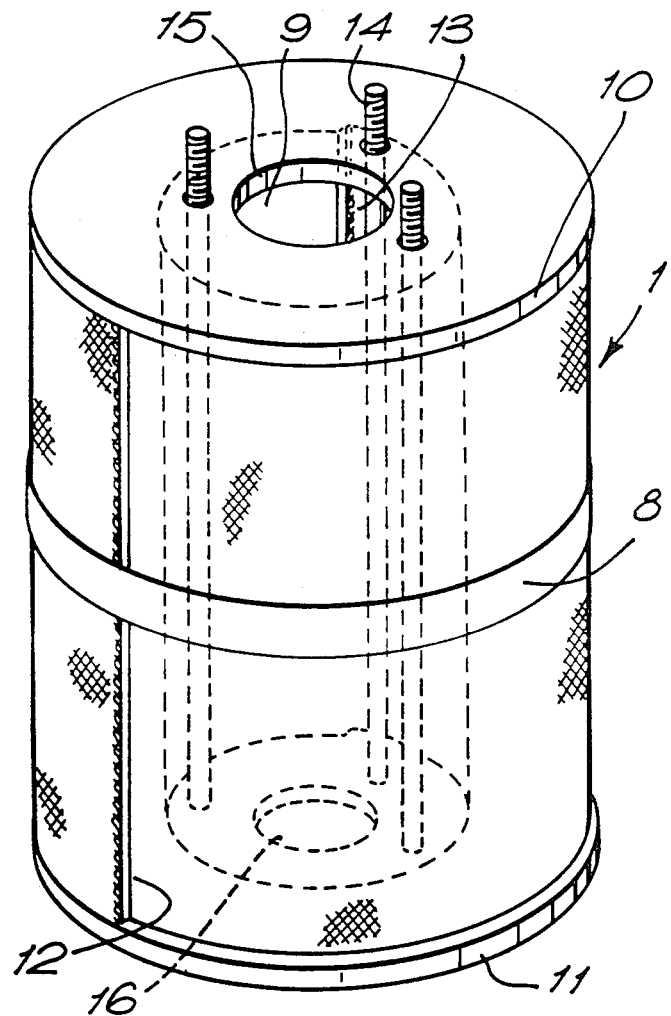

VAPORIZERS AND WICK ASSEMBLIES THEREFOR

This invention relates to vaporizers, in particular anaesthetic vaporizers, and to wick assemblies therefor.

Various types of wick assembly are known for use in anaesthetic vaporizers. One type of known vaporizer includes a vaporizing chamber partly filled with liquid anaesthetic in which a lower portion of the wick assembly is immersed. A carrier gas stream flows over the vaporizing surface of the wick to entrain anaesthetic vapour and the mixture is then delivered to the patient. In order that the gas should become sufficiently saturated with anaesthetic vapour it must remain in contact with the vaporising surface of the wick for a long period, and this has been achieved by guiding the gas downwards via a helical path formed in an annular chamber defined by the space between two concentric cylinders of wick material.

In another known vaporizer the wick assembly comprises a number of vertical, spaced apart sheets of wick material which are partly immersed in liquid anaesthetic, in which the gas flows past each such sheet via a multiplicity of horizontal passages.

However both these known wick assemblies are relatively complex in structure and fitting thereof to a vaporizer and removal for servicing can require specialist attention.

One particularly effective type of wick material, known for example from British patent No. 1043110, is metallic wire cloth. The capillary action of such cloth can be greatly enhanced by securing it in contact with a smooth unperforated metal surface, due to the formation of additional small upwardly directed passages between the wires of the mesh and the surface of the metal plate.

Viewed from one aspect the invention provides a wick assembly for a vaporizer, such assembly comprising an absorbent wick material provided with a substantially impermeable backing layer, the wick material and the backing layer being rolled into a substantially spiral configuration so as to define a substantially spiral flow passage extending through the assembly, fastening means being provided to hold said wick material and backing layer in such spiral configuration whereby the assembly forms a self-contained unit adapted to be detachably mounted in a vapouriser.

With a wick assembly in accordance with the invention a flow passage of sufficient length to provide a desired degree of vapour saturation may be achieved with a relatively simple wick structure.

Generally, the wick assembly will be rolled into the spiral configuration in such a manner that its outside shape is generally cylindrical i.e. having a circular outer cross-section which exhibits internally the spiral configuration. However it is possible for the precise configuration of the spiral to vary such that the cross-section of the cylinder can be any convenient shape. For example it may be oval or elliptical, or possibly square or rectangular.

In use in a vaporizer, one longitudinal end of the wick assembly is immersed in a liquid which is drawn up through the wick material by capillary action, such action being assisted by the presence of the backing layer since this provides additional upward passages defined between the absorbent material and the impermeable layer. The drawing up may take place along substantially the whole length of the spiral. A stream of carrier gas is then passed from one end of the spiral to the other, either from the outside thereof to the centre or vice versa, via the spiral flow passage and the carrier becomes saturated with vapour due to its prolonged contact with the wick material carrying the liquid. The wick assembly is particularly suitable for use in an anaesthetic vapouriser, in which case the liquid is a suitable anaesthetic agent.

Since the assembly is a self-contained unit it may be mounted in a vapouriser in an interchangeable manner, and the wick assembly may thus be readily replaced and/or removed for servicing as necessary and this represents a significant practical advantage.

The wick material is preferably in sheet form and may comprise a plurality of sheets spaced at intervals or adjacent each other along the length of the spiral. Preferably, however, the wick material comprises a single continuous sheet. Although the wick material and the backing layer may be of any suitable configuration to suit vaporizing requirements, in one preferred arrangement the wick assembly is fabricated from a strip of wick material and impermeable backing layer whose length is substantially longer than its width, for example a length twenty times longer than the width. This results in a spiral flow passage which is twenty times longer than the height of the wick assembly, so that in use a high degree of saturation of the carrier gas with vapour is obtained, while at the same time the wick assembly as a whole is particularly compact and easy to handle and install.

The wick material should be selected to ensure that e.g. an anaesthetic agent to be evaporated is spread in a thin liquid film over a large vaporizing surface of the wick assembly. It should therefore have a good capillary action in order to provide a liquid film extending a substantial distance above the surface of the liquid and it should also have good heat conductivity so as to transfer heat from the environment to offset the cooling effect of evaporation. A further requirement is of course that the material should be inert to the liquid intended to be vaporized, and one suitable material is fine metallic wire cloth, made for example of stainless steel, Monel (registered trade mark) metal or phosphor bronze. Although various types of cloth weave are suitable, good results are obtained by arranging the cloth so that strands of the weave extend both at right angles to the length of the spiral (vertically in use) and also along the length of the spiral (horizontally in use), and one preferred weave is Hollander twill. Preferably, more strands extend at right angles to the length of the spiral than extend along its length.

The impermeable backing layer may take any convenient form, for example an impermeable coating provided on one surface of the wick material. Preferably, however, the backing layer is formed of a separate sheet of material secured to the wick material by suitable means e.g. spot welding. The backing material should be inert to the liquid concerned and is preferably a good heat conductor; stainless steel is thus particularly suitable.

The spiral flow passage defined on each side by opposed portions of the backing layer, in which the wick material is disposed, should neither be so narrow that there is an undesirable resistance to flow of carrier gas, nor should it be so wide that a proportion of the gas can flow along the passage without being in good contact with the wick material. In order to obtain the desired passage width suitable spacing means can be provided, and to this end, for example, spacing inserts arranged at intervals along the passage. Preferably however the backing layer is dimpled at intervals to form projections so that the spacing of opposed portions of the backing layer is at least the height of such projections. It is possible for the projections to protrude from the backing layer through spaces in the wick material, but in a preferred arrangement the wick material is in contact with the face of the backing layer on which the dimples are re-entrant. The spiral configuration can then be arranged so that the projections protrude from the backing layer across the spiral passage to just touch the opposed wick material, and if the projections are all of the same size then the spiral passage will have a uniform width.

Preferably, wick material in sheet form and the backing layer are secured to each other generally uniformly over the whole of their mating faces. The spiral configuration is advantageously arranged such that the sheet of wick material is disposed on the outwardly facing curved surface of the backing layer so that the wick material is stretched as the assembly is rolled into a spiral, thereby assisting good capillary action and good thermal contact with the backing layer.

The wick material and the backing layer will generally be initially flat and during fabrication are rolled into the spiral configuration, and there may then be a tendency for the assembly to unroll itself. It is thus necessary to provide the fastening means to prevent such unrolling; such means may comprise for example welds, one or more clips, or rivets at the outer end of the spiral, but in a particularly effective arrangement a retaining band or clip extends round the outside of the assembly to retain the spiral configuration. Such retaining means is desirable even if there is no tendency to unroll, to improve generally the ease of handling of the assembly in the form of a self-contained unit.

In order that the wick assembly can be readily serviced or replaced in e.g. an anaesthetic vaporizer, it should include suitable mounting means. Preferably the mounting means includes a clamping member arranged perpendicularly to the longitudinal axis of the wick assembly and abutting one longitudinal end thereof, and one or more fixing element extending through the assembly from said member to the other longitudinal end thereof, such fixing element(s) being adapted detachably to mount the assembly to a vaporizer e.g. by being screw threaded. The clamping member can be of any suitable shape to serve as an abutment against one spiral edge of the wick material and backing layer. In a preferred such embodiment, a first closure plate substantially covers one end of the assembly and includes a central aperture e.g. for the entry of liquid to be vaporized, a second closure plate being provided substantially covering the other end of the assembly and having an aperture e.g. for the exit of vapour saturated carrier gas, and said fixing element comprising at least one fixing bolt connecting said first and second closure plates. Such an arrangement provides a readily manageable unit having structural integrity which can for example be easily located and detachably mounted in a vaporizing chamber of an anaesthetic vaporizer.

Viewed from another aspect the invention provides a method of manufacturing a wick assembly for a vaporizer, comprising providing a layer of absorbent wick material with a substantially impermeable backing layer, rolling said layers into a substantially spiral configuration, and fastening said layers in such configuration whereby said assembly forms a self-contained unit adapted to be detachably mounted in a vapouriser.

The rolling will generally be accomplished by gripping one end of the backing layer which is to form the centre of the spiral and rotating this end, either manually or mechanically. In a preferred method, the backing layer is in the form of a separate sheet and is provided at one end with a drive tag bent away from the layer of wick material, and this drive tag is gripped and rotated to roll up the assembly, for example by using a rolling tool having a slot for receiving the drive tag. One or more such drive tags may be provided along said end of the backing layer, but preferably a single tag extends along substantially the whole of the end to ensure uniformity in the rolling action. Preferably the or each tag is removed after rolling, for example, by means of a hand saw.

It is desirable that in the spiral configuration there should be defined between opposed portions of the backing layer a passage of uniform width, and this is achieved in a preferred method by forming equally spaced dimples to form projections in the backing layer prior to securing the sheet of wick material thereto on the face thereof on which the dimples are re-entrant, and rolling the layers until each projection extends across the spiral passage to touch the opposed wick material.

The fastening of the assembly in a spiral configuration may be achieved by means of, e.g., welding or a suitable band or clip as discussed above.

Viewed from another aspect, the invention provides a vaporizer including a detachable wick assembly as discussed above.

In such a vaporizer an advantageously prolonged contact between the carrier gas and the wick material can be achieved by means of the spiral passage, thereby ensuring that the carrier becomes saturated with e.g. anaesthetic vapour. The vaporizer can be a plenum vaporizer operating under a positive carrier gas pressure generally supplied from a cylinder, or it can be a draw-over type inhaler operated by the breathing of a patient which draws air or oxygen enriched air through the vaporizer.

Generally the vaporizer will include a vaporizing chamber adapted to receive e.g. liquid anaesthetic agent and in which the wick assembly is disposed. The vaporizer preferably includes inlet means for the entry of carrier gas to said vaporizing chamber, and outlet means for the exit of saturated carrier gas from the chamber, wherein the gas flows in use between the inlet and outlet means via the spiral passage. In a preferred arrangement the wick assembly is arranged for the gas to enter the spiral passage at the outside thereof and to flow to the centre thereof, the wick assembly being mounted to a wall of the vaporizing chamber in sealing engagement therewith to permit gas flow from the wick assembly centre out of the vaporizing chamber.

An embodiment of the invention in its various aspects will now be described by way of example with reference to the accompanying drawings in which:

FIGS. 1(a), (b) and (c) show respectively a strip of wick material, a backing strip and the two strips in face-to-face contact;

FIG. 2(a) is a plan view of the strips in a spiral configuration and FIG. 2(b) shows a portion of the tightened spiral;

FIG. 3 is a schematic perspective view of the wick assembly ready for mounting in an anaesthetic vaporizer.

Figure 4:
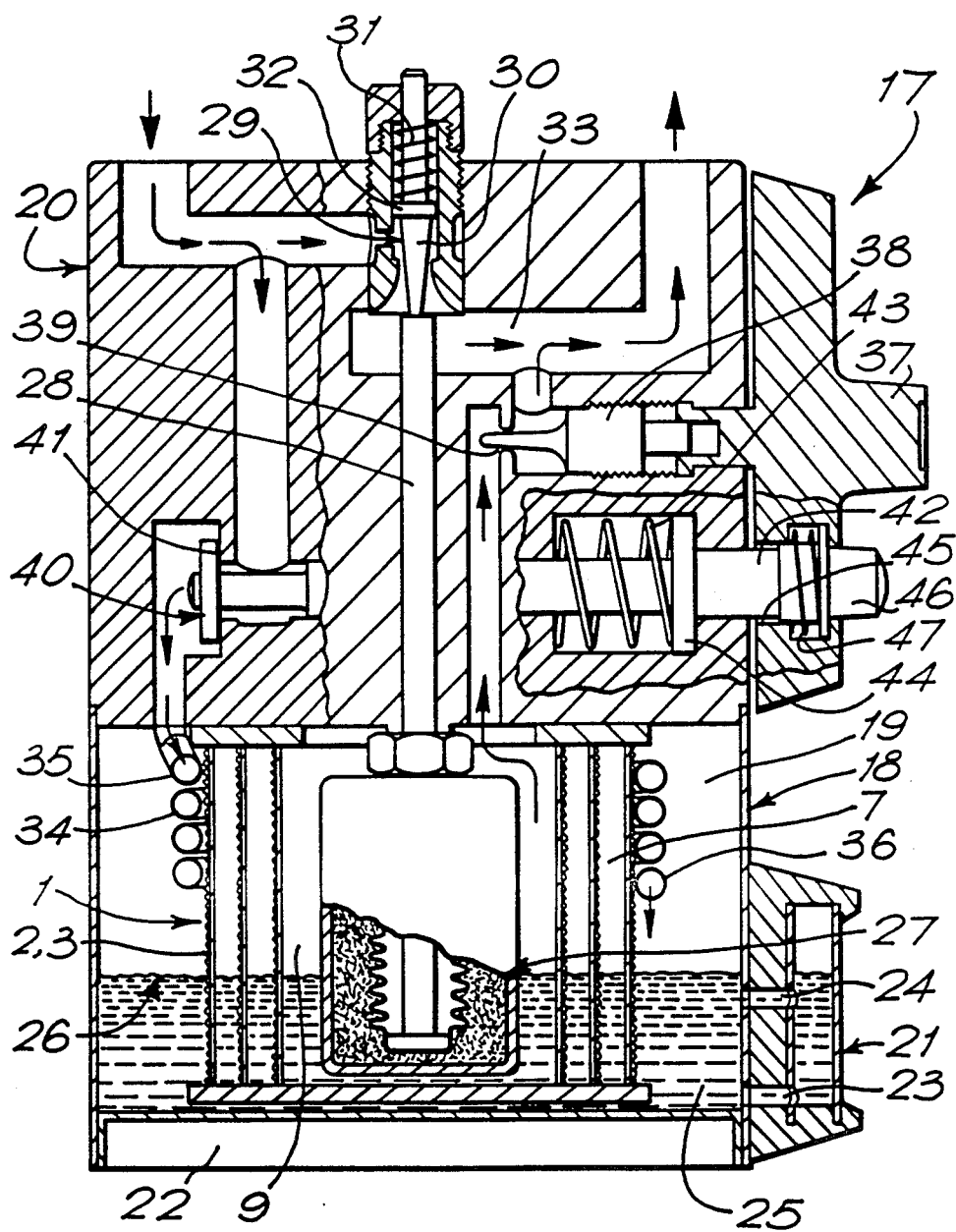
FIG. 4 is a schematic cross-sectional view of an anaesthetic vaporizer in which the wick assembly is mounted.

The wick assembly 1 shown in FIG. 3 is manufactured as follows. Referring to FIG. 1(a), a straight strip 2 is cut from a sheet of suitable wick material. FIG. 1(b) shows a backing strip 3 cut from a solid sheet of stainless steel to a length slightly longer than the wick material strip 2. Typical dimensions of the two strips are a length of about 1000 mm and a width of about 50 mm. The backing strip is dimpled by punching to form two parallel rows of projections adjacent each straight edge of the strip, the projections being spaced at about 30 mm intervals and projecting outwardly by about 2 mm. The wick material strip 2 is then spot-welded to the backing strip 3 on its face without projections as shown in FIG. 1(c) and the longer end of the backing strip is bent away from the wick material to form a drive tag 5.

The drive tag is gripped and rotated thereby rolling the pair of strips into a spiral configuration 6 having an overall cylindrical shape with the drive tag at the centre, as shown in FIG. 2(a). The spiral is formed with the wick material on the outside of the backing strip so that the wick material is stretched by the rolling process and remains in pre-stressed contact with the solid backing strip, assisting capillary action. The spiral is tightened until the inwardly protruding projections 4 extend across the spiral passage 7 to just touch the wick material strip 2, as shown in FIG. 2(b), thereby ensuring that the passage 7 is of uniform width throughout its length. Referring to FIG. 3, when the spiral 6 is of the desired tightness a retaining band 8 is fitted round the periphery thereof, and the drive tag 5 is then removed by means of a hand saw to provide an axial cavity 9 in the centre of the spiral.

Two end closure plates 10 and 11 are sealed to the top and bottom respectively of the spiral so that the spiral passage 7 defined between adjacent portions of the backing strip extends about 1000 mm from an outside rectangular opening 12 to an inner rectangular opening 13 in the centre of the spiral. The closure plates are held in position by three fixing bolts 14 which extend from the bottom plate 11 through the assembly to the top plate 10 from which they project upwardly. Suitable apertures are provided in the closure plates to receive the fixing bolts, while top plate 10 includes an opening 15 for the passage of carrier gas and the bottom plate 11 includes an opening 16 for the entry and drainage of liquid anaesthetic agent. The projecting fixing bolts 14 are used to secure the wick assembly to an anaesthetic vaporizer. It will be seen that the wick assembly forms a self-contained unit which may readily be secured within a vapouriser by means of the bolts 14, enabling easy removal of the assembly for servicing and/or replacement when required.

The anaesthetic vaporizer 17 shown in FIG. 4 is a plemunm vaporizer comprising a bodv 18 within which is a vaporizing chamber 19, a head 20 mounted on the body and housing the control structure of the vaporizer, a wick assembly 1 suspended from the head 20, and a liquid level indicator and filler unit 21.

The body 18 which is of stainless steel is cylindrical in shape and is closed at its lower end by a sealing member 22. The liquid level indicator and filler unit 21 communicates with the vaporizing chamber 19 at two points 23 and 24 to permit filling of the chamber with liquid anaesthetic agent 25 and to give an indication of the liquid level 26.

Inside the vaporizing chamber 19 and partly immersed in the liquid the wick assembly 1 is secured to the head 20 by means of fixing bolts 14 (not shown in FIG. 4). The wick assembly has more turns in its spiral than are actually shown in FIG. 4. In the axial cavity 9 of the wick assembly there is secured to the head 20 a mechanical temperature sensitive device 27 the output of which is a push rod 28 which is moved upwards or downwards in accordance with temperature changes. A bypass orifice valve 29 in the control structure of the vaporizer includes a valve member 30 biassed into engagement with the push rod 28 by means of a compression spring 31 bearing on an annular flange 32 of the valve member. The position of the valve member 30 controls the proportion of carrier gas which passes through a bypass passage 33 instead of through the vaporizing chamber 19.

Secured to the head 20 of the vaporizer is a helical tube 34 extending round the outside of the wick assembly. The helical tube has an inlet end 35 for the entry of carrier gas and an outlet end 36 for the discharge of carrier gas after it has travelled the length of the helix. One purpose of the helical tube is to allow the temperature of the gas to adjust to that of the vaporizing chamber before coming into contact with the anaesthetic agent. Thus the temperature of the gas discharged from outlet end 36 of the helical tube will be close to that sensed by the temperature sensing device 27.

A control knob 37 in the head 20 of the vaporizer is provided to control the flow of gas from the vaporizing chamber. The control knob engages with a needle valve member 38 such that rotation of the knob results in axial movement of the valve member to open or close an anaesthetic control orifice 39 in the outlet path from the vaporizing chamber. The control knob also engages with a zero lock mechanism 40 which ensure that when control orifice 39 is closed then a zero lock port 41 upstream of the vaporizing chamber is also closed, the closed position being shown in FIG. 4.

The zero lock mechanism includes a locking member 42 biased rightwardly as illustrated by means of a compression spring 43 engaging an annular flange 44 of the locking member to close zero lock port 41. In the locked position the locking member is displaced fully to the right and engages in a locking aperture 45 of the control knob 37. When it is desired to pass gas through the vaporizing chamber the control knob 37 must be rotated to open control orifice 39, and this is accomplished by depressing a zero lock push button 46 against the force of a compression spring 47, the push button then pressing against the locking member 42 to move it to the left out of locking engagement with aperture 45 so that the control knob 37 can be rotated. The leftward movement of locking member 42 opens the zero lock port 41 and once the aperture 45 in the control knob is rotated out of alignment with the locking member then the latter is held in its leftward position to maintain the zero lock port open. Thus the zero lock port 41 is fully open while control knob 37 controls the extent to which the anaesthetic control orifice 39 is open. When the control knob is moved to close the control orifice then the locking member 42 returns into engagement with the locking aperture 45 to close the zero lock port 41.

The operation of the anaesthetic vaporizer is as follows. When the control knob 37 is actuated to open both the zero lock port 41 and the control orifice 39 then carrier gas flows through the helical tube 34 into the vaporizing chamber. The gas first comes into contact with the surface 26 of the liquid anaesthetic agent and the film of such liquid which has been drawn up into the wick material on the peripheral surface of the wick assembly 1. It enters the spiral passage 7 of the wick assembly through the rectangular opening 12 and flows radially inwardly along the passage 7 defined between opposed portions of the backing strip 3. Along this passage it is in contact with the vaporizing surface of the wick along the whole of the length thereof to become saturated with anaesthetic agent, and the saturated gas emerges from the passage through the central rectangular opening 13. It passes from axial cavity 9 up through the head 20 of the vaporizer via the control orifice 39 to be discharged and delivered to the patient.

When the liquid anaesthetic vaporizes there is an associated drop in temperature due to the heat required for vaporization, leading to a decrease in vapour pressure. There is thus a potential problem that the concentration of anaesthetic in the carrier gas will decrease, but this problem is met by automatically compensating for temperature changes. As the temperature drops the mechanical temperature sensitive device 27 permits spring 31 to push valve member 30 downwards to close the bypass orifice valve 29 so that a larger proportion of carrier gas flows through the vaporizing chamber rather than being fed through the bypass passage 33. Thus the concentration of anaesthetic agent is maintained despite the drop in temperature.

We claim:

1. A wick assembly for a vaporizer, such assembly comprising an absorbent wick material provided with a substantially impermeable backing sheet, the wick material and the backing sheet being disposed in a substantially spiral configuration so as to define a substantially spiral flow passage extending through the assembly, the spiral configuration being formed by mating together the wick material and backing sheet in face to face relationship and rolling them into the spiral configuration with the wick material disposed on an outwardly facing convex side of the backing sheet, so that in a rolled assembly the wick material is stretched into intimate contact with the backing sheet, fastening means being provided to hold said wick material and backing sheet in such spiral configuration, and means for detachably mounting the assembly in a vaporizer.

2. A wick assembly as claimed in claim 1, wherein the wick material and the backing sheet are each in the form of elongate strips and are secured together substantially uniformly over the length of their mating faces.

3. A wick assembly as claimed in claim 1, including spacing means arranged between successive turns of said wick material and backing sheet to maintain a minimum width of said spiral flow passage.

4. A wick assembly as claimed in claim 3, wherein the spacing means comprises dimples in said backing sheet.

5. A wick assembly as claimed in claim 1, wherein the fastening means comprises a retaining element extending around the outside of the assembly.

6. A vaporizer including a detachable wick assembly as set out in claim 1.

7. A wick assembly for a vaporizer, such assembly comprising an absorbent wick material formed of metallic wire cloth provided with a substantially impermeable metallic backing sheet, the wick and the backing sheet being disposed in a substantially spiral configuration so as to define a substantially spiral flow passage extending through the assembly, the spiral configuration being formed by mating together the wick material and backing sheet in face to face relationship and rolling them into the spiral configuration with the wick material disposed on an outwardly facing convex side of the backing sheet, so that in a rolled assembly the metallic wick material is stretched into intimate contact with the metallic backing sheet, fastening means being provided to hold said wick material and backing sheet in such spiral configuration, and means for detachably mounting the assembly in a vaporizer.

8. A wick assembly as claimed in claim 7, wherein the wick material and the backing sheet are each in the form of elongate strips and are secured together substantially uniformly over the length of their mating faces.

9. A wick assembly as claimed in claim 7, including spacing means arranged between successive turns of said wick material and backing sheet to maintain a minimum width of said spiral flow passage.

10. A wick assembly as claimed in claim 9, wherein the spacing means comprises dimples in said backing sheet.

11. A wick assembly as claimed in claim 7, wherein the fastening means comprises a retaining element extending around the outside of the assembly.

12. A vaporizer including a detachable wick assembly as set out in claim 7.

13. A wick assembly for a vaporizer, such assembly comprising an absorbent wick material formed of metallic wire cloth provided with a substantially impermeable metallic backing sheet, the wick material and the backing sheet being disposed in a substantially spiral configuration so as to define a substantially spiral flow passage extending through the assembly, the spiral configuration being formed by mating together the wick material and the backing sheet in face to face relationship and rolling them into the spiral configuration with the wick material disposed on an outwardly facing convex side of the backing sheet, so that in a rolled assembly the metallic wick material is stretched into intimate contact with the metallic backing sheet, the assembly further comprising fastening means to hold said wick material and backing sheet in such spiral configuration, a first closure plate abutting one longitudinal end of the spiral configuration, a second closure plate abutting another longitudinal end of the spiral configuration, such plates including openings which respectively permit entry of liquid to be vaporized into the assembly and exit from the assembly of vapor saturated gas, and at least one fixing element extending longitudinally through the assembly between the first and second closure plates so that the spiral configuration of said wick material and said backing sheet is clamped between the plates, the fixing element having a free end for detachably securing the assembly to attachment means provided within a vaporizer, whereby the assembly forms a self-contained unit for detachable mounting in a vaporizer.

14. A wick assembly as claimed in claim 13, wherein the wick material and the backing sheet are in the form of elongate strips and are secured together substantially uniformly over the length of their mating faces.

15. A wick assembly as claimed in claim 13, including spacing means arranged between successive turns of said wick material and backing sheet to maintain a minimum width of said spiral flow passage.

16. A wick assembly as claimed in claim 15, wherein the spacing means comprises dimples in said backing sheet.

17. A wick assembly as claimed in claim 13, wherein the fastening means comprises a retaining element extending around the outside of the assembly.

18. A vaporizeer including a detachable wick assembly as set out in claim 13.

19. A method of manufacturing a wick assembly for a vaporizer, the method comprising providing a layer of absorbent wick material, providing a substantially impermeable backing sheet, mating together the wick material and backing sheet in face to face relationship, rolling the mated wick material and backing sheet into a substantially sprial configuration so as to define a substantially spiral flow passage extending through the assembly, the wick material being disposed on an outwardly facing convex side of the backing sheet, so that in a rolled assembly the wick material is stretched into intimate contact with the backing sheet, fastening the wick material and backing sheet in said spiral configuration, and providing means for detachably mounting the assembly in a vaporizer.

20. A method of manufacturing a wick assembly for a vaporizer, the method comprising providing a layer of absorbent wick material formed of metallic wire cloth, providing a substantially impermeable metallic backing sheet, mating together the wick material and backing sheet in face to face relationship, rolling the mated wick material and backing sheet into a substantiaily spiral configuration so as to define a substantially spiral flow passage extending through the assembly, the wick material being disposed on an outwardly facing convex side of the backing sheet, so that in a rolled assembly the metallic wick material is stretched into intimate contact with the metallic backing sheet, fastening the wick material and backing sheet in said spiral configuration, and providing means for detachably mounting the assembly in a vaporizer.

21. A method of manufacturing a wick assembly for a vaporizer, the method comprising providing a layer of absorbent wick material formed of metallic wire cloth, providing a substantially impermeable metallic backing sheet, mating together the wick material and kbacking sheet in face to face relationship, rolling the mated wick material and backing sheet into a substantially spiral flow configuration so as to define a substantially spiral flow passage extending through the assembly, the wick material being disposed on an outwardly facing convex side of the backing sheet so that in the rolled assembly the metallic wick material is stretched into intimate contact with the metallic backing sheet, fastening the wick material and backing sheet in said spiral configuration, providing a first closure plate abutting one longitudinal end of the spiral configuration, providing a second closure plate abutting another longitudinal end of the spiral configuration, such plates including openings which respectively permit entry of liquid to be vaporized into the assembly and exit from the assembly of vapor saturated gas, and providing at least one fixing element extending longitudinally through the assembly between the first and second closure plates so that the spiral configuration of said wick material and said backing sheet is clamped between the plates, the fixing element having a free end for detachably securing the assembly to attachment means provided within a vaporizer, whereby the assembly forms a self-contained unit for detachable mounting in a vaporizer.

* * * * *